United States Patent [19]

Payne et al.

[11] Patent Number: 5,169,629
[45] Date of Patent: Dec. 8, 1992

[54] **PROCESS OF CONTROLLING LEPIDOPTERAN PESTS, USING *BACILLUS THURINGIENSIS* ISOLATE DENOTED B.T PS81GG**

[75] Inventors: Jewel Payne; August J. Sick, both of San Diego; Mark Thompson, Del Mar, all of Calif.

[73] Assignee: Mycogen Corporation, San Diego, Calif.

[21] Appl. No.: 265,731

[22] Filed: Nov. 1, 1988

[51] Int. Cl.$^5$ .................... A01N 63/00; C12N 1/20; C12N 15/32

[52] U.S. Cl. .................... 424/93 L; 435/252.5; 935/6; 935/9; 935/22; 935/59; 935/66; 935/72

[58] Field of Search ............ 424/93; 536/27; 435/69.1, 71.1, 91, 170, 172.1, 172.3, 252.1, 252.3, 252.5, 320.1; 935/6, 9, 22, 59, 66, 72

[56] References Cited

U.S. PATENT DOCUMENTS

| | | | |
|---|---|---|---|
| 4,448,885 | 5/1984 | Schnepf et al. | 435/253 |
| 4,467,036 | 8/1984 | Schnepf et al. | 435/317 |
| 4,902,507 | 2/1990 | Morris et al. | 424/93 |
| 4,910,016 | 3/1990 | Gaertner et al. | 424/93 |

OTHER PUBLICATIONS

Adang et al., 1985, *Gene*, vol. 36: 289-300.
Schnepf, H. E., and H. R. Whitely (1981) "Cloning and Expression of the *Bacillus thuringiensis* Crystal Protein Gene in *Escherichia coli*", Proc. Natl. Acad. Sci. USA 76(5):2893-2897.
Yoshida, H. A., and M. P. Parrella (1987) "The Beet Armyworm in Floricultural Crops", California Agriculture 41:13-15.

*Primary Examiner*—Richard A. Schwartz
*Assistant Examiner*—Nancy Vogel
*Attorney, Agent, or Firm*—Saliwanchik & Saliwanchik

[57] ABSTRACT

A novel *B.t.* isolate with activity against lepidopteran insects is disclosed. This isolate is highly active agaist the beet armyworm. A gene from this isolate has been cloned. The DNA encoding the *B.t.* toxin can be used to transform various prokaryotic and eukaryotic microbes to express the *B.t.* toxin. These recombinant microbes can be used to control lepidopteran insects in various environments.

11 Claims, 25 Drawing Sheets

A. B.t. PS81GG uncut
B. B.t. PS81GG cut with HindIII
C. B.t. HD-1 uncut
D. B.t. HD-1 cut with HindIII

Figure 2A

```
              10         20         30         40         50         60
  1  ATGGATAACA ATCCGAACAT CAATGAATGC ATTCCTTATA ATTGTTTAAG TAACCCTGAA
 61  GTAGAAGTAT TAGGTGGAGA AAGAATAGAA ACTGGTTACA CCCAATCGA TATTTCCTTG
121  TCGCTAACGC AATTCTTTT GAGTGAATTT GTTCCCGGTG CTGGATTGT GTTAGGACTA
181  GTTGATATAA TATGGGAAT TTTTGGTCCC TCTCAATGGG ACGCATTTCT TGTACAAATT
241  GAACAGTTAA TTAACCAAAG AATAGAAGAA TTCGCTAGGA ACCAAGCCAT TTCTAGATTA
301  GAAGGACTAA GCAATCTTTA TCAAATTTAC GCAGAATCTT TTAGAGAGTG GGAAGCAGAT
361  CCTACTAATC CAGCATTAAG AGAAGAGATG CGTATTCAAT TCAATGACAT GAACAGTGCC
421  CTTACAACCG CTATTCCTCT TTTGGCAGTT CAAATTATC AAGTTCCTCT TTTATCAGTA
481  TATGTTCAAG CTGCAAATTT ACATTATCA GTTTTTGAGAG ATGTTTCAGT GTTTGGACAA
541  AGGTGGGGAT TTGATGCCGC GACTATCAAT AGTCGTTATA ATGATTTAAC TAGGCTTATT
              610        620        630        640        650        660
601  GGCAACTATA CAGATTATGC TGTACGCTGG TACAATACGG GATTAGAACG TGTATGGGGA
661  CCGGATTCTA GAGATTGGGT AAGGTATAAT CAATTAGAA GAGAATTAAC ACTAACTGTA
721  TTAGATATCG TTGCTCTGTT CCCGAATTAT GATAGTAGAA GATATCCAAT TCGAACAGTT
781  TCCCAATTAA CAAGAGAAAT TTATACAAAC CCAGTATTAG AAAATTTGA TGGTAGTTTT
841  CGAGGCTCGG CTCAGGGCAT AGAAAGAAGT ATTAGGAGTC CACATTTGAT GGATATACTT
```

Figure 2A

```
        910        920        930        940        950        960
 901 AACAGTATAA CCATCTATAC GGATGCTCAT AGGGGTTATT ATTATTGGTC AGGGCATCAA
 961 ATAATGGCTT CTCCTGTCGG TTTTTCGGGG CCAGAATTCA CGTTTCCGCT ATATGGAACC
1021 ATGGAAATG CAGCTCCACA ACAACGTATT GTTGCTCAAC TAGGTCAGGG CGTGTATAGA
1081 ACATTATCCT CTACTTTTTA TAGAAGACCT TTTAATATAG GGATAAATAA TCAACAACTA
1141 TCTGTTCTTG ACGGGACAGA ATTTGCTTAT GGAACCTCCT CAAATTTGCC ATCCGCTGTA 1210       1220       1230       1240       1250       1260
1201 TACAGAAAAA GCGGAACGGT AGATTCGCTG GATGAAATAC CACCACAGAA TAACAACGTG
1261 CCACCTAGGC AAGGATTTAG TCATCGATTA AGCCATGTTT CAATGTTTCG TTCAGGCTCT
1321 AGTAGTAGTG TAAGTATAAT AAGAGCTCCT ATGTTCTCTT GGATACATCG TAGTGCTGAA
1381 TTTAATAATA TAATTGCATC GGATAGTATT ACTCAAATCC CTGCAGTGAA GGGAAACTTT
1441 CTTTTTAATG GTTCTGTAAT TTCAGGACCA GGATTACTG GTGGGGACTT AGTTAGATTA 1510       1520       1530       1540       1550       1560
1501 AATAGTAGTG GAAATAACAT TCAGAATAGA GGGTATATTG AAGTTCCAAT TCACTTCCCA
1561 TCGACATCTA CCAGATATCG AGTTCGTGTA CGGTATGCTT CTGTAACCCC GATTCACCTC
1621 AACGTTAATT GGGGTAATTC ATCCATTTTT TCCAATACAG TACCAGCTAC AGCTACGTCA
1681 TTAGATAATC TACAATCAAG TGATTTTGGT TATTTTGAAA GTGCCAATGC TTTTACATCT
1741 TCATTAGGTA ATATAGTAGG TGTTAGAAAT TTTAGTGGGA CTGCAGGAGT GATAATAGAC
```

Figure 2B

```
1801 AGATTTGAAT TTATTCCAGT TACTGCAACA CTCGAGGCTG AATATAAATCT GGAAAGAGCG
1861 CAGAAGGCGG TGAATGCGCT GTTTACGTCT ACAAACCAAC TAGGGCTAAA AACAAATGTA
1921 ACGGATTATC ATATTGATCA AGTGTCCAAT TTAGTTACGT ATTTATCGGA TGAATTTGT
1981 CTGGATGAAA AGCGAGAATT GTCCGAGAAA GTCAAACATG CGAAGCGACT CAGTGATGAA
2041 CGCAATTTAC TCCAAGATTC AAATTTCAAA GACATTAATA GGCAACCAGA ACGTGGGTGG 1820       1830       1840       1850       1860

2101 GGCGGAAGTA CAGGGATTAC CATCCAAGGA GGGGATGACG TATTTAAAGA AAATTACGTC
2161 ACACTATCAG GTACCTTTGA TGAGTGCTAT CCAACATATT TGTATCAAAA AATCGATGAA
2221 TCAAAATTAA AAGCCTTTAC CCGTTATCAA TTAAGAGGGT ATATCGAAGA TAGTCAAGAC
2281 TTAGAAATCT ATTTAATTCG CTACAATGCA AAACATGAAA CAGTAAATGT GCCAGGTACG
2341 GGTTCCTTAT GGCCGCTTTC AGCCCAAAGT CCAATCGGAA AGTGTGGAGA GCCGAATCGA 2120       2130       2140       2150       2160

2401 TGCGGCCCAC ACCTTGAATG GAATCCTGAC TTAGATTGTT CGTGTAGGGA TGGAGAAAAG
2461 TGTGCCCATC ATTCGCATCA TTTCTCCTTA GACATTGATG TAGGATGTAC AGACTTAAAT
2521 GAGGACCTAG GTGTATGGGT GATCTTTAAG ATTAAGAGCC AAGATGGGCA CGCAAGACTA
2581 GGGAATCTAG AGTTTCTCGA AGAGAAACCA TTAGTAGGAG AAGCGCTAGC TCGTGTGAAA
2641 AGAGCGGAGA AAAAATGGAG AGACAAACGT GAAAAATTGG AATGGGAAAC AAATATCGTT 2420       2430       2440       2450       2460
```

Figure 2C

```
           2710       2720       2730       2740       2750       2760
2701 TATAAAGAGG CAAAAGAATC TGTAGATGCT TTATTTGTAA ACTCTCAATA TGATCAATTA
2761 CAAGCGGATA CGAATATTGC CATGATTCAT GCGGCAGATA AACGTGTTCA TAGCATTCGA
2821 GAAGCTTATC TGCCTGAGCT GTCTGTGATT CCGGGTGTCA ATGCGGCTAT TTTTGAAGAA
2881 TTAGAAGGGC GTATTTTCAC TGCATTCTCC CTATATGATG CGAGAAATGT CATTAAAAAT
2941 GGTGATTTTA ATAATGGCTT ATCCTGCTGG AACGTGAAAG GGCATGTAGA TGTAGAAGAA 3010       3020       3030       3040       3050       3060
3001 CAAACAACC  AACGTTCGGT CCTTGTTGTT CCGGAATGGG AAGCAGAAGT GTCACAAGAA
3061 GTTCGTGTCT GTCCGGGTCG TGGCTATATC CTTCGTGTCA CAGCGTACAA GGAGGGATAT
3121 GGAGAAGGTT GCGTAACCAT TCATGAGATC GAGAACAATA CAGACGAACT GAAGTTTAGC
3181 AACTGCGTAG AAGAGGAAAT CTATCCAAAT AACACGGGTA CGTGTAATGA TTATACTGTA
3241 AATCAAGAAG AATACGGAGG TGCGTACACT TCTCGTAATC GAGGATATAA CGAAGCTCCT 3310       3320       3330       3340       3350       3360
3301 TCCGTACCAG CTGATTATGC GTCAGTCTAT GAAGAAAAAT CGTATACAGA TGGACGAAGA
3361 GAGAATCCTT GTGAATTTAA CAGAGGGTAT AGGGATTACA CGCCACTACC AGTTGGTTAT
3421 GTGACAAAAG AATTAGAATA CTTCCCAGAA ACCGATAAGG TATGGATTGA GATTGGAGAA
3481 ACGGAAGGAA CATTTATCGT GGACAGCGTG GAATTACTCC TTATGGAGGA A*
```

Segment 1-3531

Figure 2D

```
                                    5                    10                   15
  1  Met Asp Asn Asn Pro Asn Ile Asn Glu Cys Ile Pro Tyr Asn Cys
 16  Leu Ser Asn Pro Glu Val Glu Val Leu Gly Gly Glu Arg Ile Glu
 31  Thr Gly Tyr Thr Pro Ile Asp Ile Ser Leu Ser Leu Thr Gln Phe
 46  Leu Leu Ser Glu Phe Val Pro Gly Ala Gly Phe Val Leu Gly Leu
 61  Val Asp Ile Ile Trp Gly Ile Phe Gly Pro Ser Gln Trp Asp Ala
 76  Phe Leu Val Gln Ile Glu Gln Leu Ile Asn Gln Arg Ile Glu Glu
 91  Phe Ala Arg Asn Gln Ala Ile Ser Arg Leu Glu Gly Leu Ser Asn
106  Leu Tyr Gln Ile Tyr Ala Glu Ser Phe Arg Glu Trp Glu Ala Asp
121  Pro Thr Asn Pro Ala Leu Arg Glu Glu Met Arg Ile Gln Phe Asn
136  Asp Met Asn Ser Ala Leu Thr Thr Ala Ile Pro Leu Leu Ala Val
151  Gln Asn Tyr Gln Val Pro Leu Leu Ser Val Tyr Val Gln Ala Ala
166  Asn Leu His Leu Ser Val Leu Arg Asp Val Ser Val Phe Gly Gln
181  Arg Trp Gly Phe Asp Ala Ala Thr Ile Asn Ser Arg Tyr Asn Asp
196  Leu Thr Arg Leu Ile Gly Asn Tyr Thr Asp Tyr Ala Val Arg Trp
211  Tyr Asn Thr Gly Leu Glu Arg Val Trp Gly Pro Asp Ser Arg Asp
226  Trp Val Arg Tyr Asn Gln Phe Arg Arg Glu Leu Thr Leu Thr Val
```

Figure 3A

| | | | | | | | | | | |
|---|---|---|---|---|---|---|---|---|---|---|
| 241 | Leu | Asp | Ile | Val | Ala | Leu | Phe | Pro | Asn | Tyr | Asp | Ser | Arg | Arg | Tyr |
| 256 | Pro | Ile | Arg | Thr | Val | Ser | Gln | Leu | Thr | Arg | Glu | Ile | Tyr | Thr | Asn |
| 271 | Pro | Val | Leu | Glu | Asn | Phe | Asp | Gly | Ser | Phe | Arg | Gly | Ser | Ala | Gln |
| 286 | Gly | Ile | Glu | Arg | Ser | Ile | Arg | Ser | Pro | His | Leu | Met | Asp | Ile | Leu |
| 301 | Asn | Ser | Ile | Thr | Ile | Tyr | Thr | Asp | Ala | His | Arg | Gly | Tyr | Tyr | Tyr |
| 316 | Trp | Ser | Gly | His | Gln | Ile | Met | Ala | Ser | Pro | Val | Gly | Phe | Ser | Gly |
| 331 | Pro | Glu | Phe | Thr | Phe | Pro | Leu | Tyr | Gly | Thr | Met | Gly | Asn | Ala | Ala |
| 346 | Pro | Gln | Gln | Arg | Ile | Val | Ala | Gln | Leu | Gly | Gln | Gly | Val | Tyr | Arg |
| 361 | Thr | Leu | Ser | Ser | Thr | Phe | Tyr | Arg | Arg | Pro | Phe | Asn | Ile | Gly | Ile |
| 376 | Asn | Asn | Gln | Gln | Leu | Ser | Val | Leu | Asp | Gly | Thr | Glu | Phe | Ala | Tyr |
| 391 | Gly | Thr | Ser | Ser | Asn | Leu | Pro | Ser | Ala | Val | Tyr | Arg | Lys | Ser | Gly |
| 406 | Thr | Val | Asp | Ser | Leu | Asp | Glu | Ile | Pro | Pro | Gln | Asn | Asn | Asn | Val |
| 421 | Pro | Pro | Arg | Gln | Gly | Phe | Ser | His | Arg | Leu | Ser | His | Val | Ser | Met |
| 436 | Phe | Arg | Ser | Gly | Phe | Ser | Asn | Ser | Ser | Val | Ser | Ile | Ile | Arg | Ala | Pro |
| 451 | Met | Phe | Ser | Trp | Ile | His | Arg | Ser | Ala | Glu | Phe | Asn | Asn | Ile | Ile |
| 466 | Ala | Ser | Asp | Ser | Ile | Thr | Gln | Ile | Pro | Ala | Val | Lys | Gly | Asn | Phe |

Figure 3B

```
481  Leu Phe Asn Gly Ser Val Ile Ser Gly Pro Gly Phe Thr Gly Gly
496  Asp Leu Val Arg Leu Asn Ser Ser Gly Asn Ile Gln Asn Arg
511  Gly Tyr Ile Glu Val Pro Ile His Phe Pro Ser Thr Ser Thr Arg
526  Tyr Arg Val Arg Val Arg Tyr Ala Ser Val Thr Pro Ile His Leu
541  Asn Val Asn Trp Gly Asn Ser Ser Ile Phe Ser Asn Thr Val Pro
556  Ala Thr Ala Thr Ser Leu Asp Asn Leu Gln Ser Ser Asp Phe Gly
571  Tyr Phe Glu Ser Ala Asn Ala Phe Thr Ser Ser Leu Gly Asn Ile
586  Val Gly Val Arg Asn Phe Ser Gly Thr Ala Gly Val Ile Ile Asp
601  Arg Phe Glu Phe Ile Pro Val Thr Ala Thr Leu Glu Ala Glu Tyr
616  Asn Leu Glu Arg Ala Gln Lys Ala Val Asn Ala Leu Phe Thr Ser
631  Thr Asn Gln Leu Gly Leu Lys Thr Asn Val Thr Asp Tyr His Ile
646  Asp Gln Val Ser Asn Leu Val Thr Tyr Leu Ser Asp Glu Phe Cys
661  Leu Asp Glu Lys Arg Glu Leu Ser Glu Lys Val Lys His Ala Lys
676  Arg Leu Ser Asp Glu Arg Asn Leu Leu Gln Asp Ser Asn Phe Lys
691  Asp Ile Asn Arg Gln Pro Glu Arg Gly Trp Gly Gly Ser Thr Gly
706  Ile Thr Ile Gln Gly Gly Asp Asp Val Phe Lys Glu Asn Tyr Val
```

Figure 3C

```
721 Thr Leu Ser Gly Thr Phe Asp Glu Cys Tyr Pro Thr Tyr Leu Tyr
736 Gln Lys Ile Asp Glu Ser Lys Leu Ala Phe Thr Arg Tyr Gln
751 Leu Arg Gly Tyr Ile Glu Asp Ser Gln Asp Leu Glu Ile Tyr Leu
766 Ile Arg Tyr Asn Ala Lys His Glu Thr Val Asn Val Pro Gly Thr
781 Gly Ser Leu Trp Pro Leu Ser Ala Gln Ser Pro Ile Ser Gly Lys Cys
796 Gly Glu Pro Asn Arg Cys Ala Pro Leu Gln His Leu Trp Asn Pro Asp
811 Leu Asp Cys Ser Cys Arg Asp Gly Lys Gly Lys Cys Ala His His Ser
826 His His Phe Ser Leu Asp Ile Asp Val Gly Cys Thr Asp Leu Asn
841 Glu Asp Leu Gly Val Trp Val Ile Phe Lys Ile Lys Thr Gln Asp
856 Gly His Ala Arg Leu Gly Asn Leu Glu Phe Leu Glu Glu Lys Pro
871 Leu Val Gly Glu Ala Leu Ala Arg Val Lys Arg Ala Glu Lys Lys
886 Trp Arg Asp Lys Arg Glu Lys Leu Glu Trp Glu Thr Asn Ile Val
901 Tyr Lys Glu Ala Lys Glu Ser Val Asp Ala Leu Phe Val Asn Ser
916 Gln Tyr Asp Gln Leu Gln Ala Asp Thr Asn Ile Ala Met Ile His
931 Ala Ala Asp Lys Arg Val His Ser Ile Arg Glu Ala Tyr Leu Pro
946 Glu Leu Ser Val Ile Pro Gly Val Asn Ala Ala Ile Phe Glu Glu
961 Leu Glu Gly Arg Ile Phe Thr Ala Phe Ser Leu Tyr Asp Ala Arg
```

Figure 3D

```
976  Asn Val Ile Lys Asn Gly Asp Phe Asn Asn Gly Leu Ser Cys Trp
991  Asn Val Lys Gly His Val Asp Val Glu Gln Asn Gln Arg
1006 Ser Val Leu Val Pro Glu Trp Glu Ala Glu Val Ser Gln Glu
1021 Val Arg Val Cys Pro Gly Arg Gly Tyr Ile Leu Arg Val Thr Ala
1036 Tyr Lys Glu Gly Tyr Gly Glu Gly Cys Val Thr Ile His Glu Ile
1051 Glu Asn Asn Thr Asp Glu Leu Lys Phe Ser Asn Cys Val Glu Glu
1066 Glu Ile Tyr Pro Asn Asn Thr Val Thr Cys Asn Asp Tyr Thr Val
1081 Asn Gln Glu Ile Gly Tyr Gly Ala Tyr Thr Ser Arg Asn Arg Gly
1096 Tyr Asn Glu Ala Pro Ser Val Pro Ala Asp Tyr Ala Ser Val Tyr
1111 Glu Lys Ser Tyr Thr Asp Gly Arg Arg Glu Asn Pro Cys Glu
1126 Phe Asn Arg Gly Tyr Arg Asp Tyr Thr Pro Leu Pro Val Gly Tyr
1141 Val Thr Lys Glu Leu Glu Tyr Phe Pro Glu Thr Asp Lys Val Trp
1156 Ile Glu Ile Gly Thr Glu Thr Gly Thr Gly Ile Val Asp Ser Val
1171 Glu Leu Leu Leu Met Glu Glu
```

Fragment 1-*

Figure 3E

```
                                      5                   10                  15                  20
Met Asp Asn Asn Pro Asn Ile Asn Glu Cys Ile Pro Tyr Asn Cys Leu Ser Asn Pro Glu
ATG GAT AAC AAT CCG AAC ATC AAT GAA TGC ATT CCT TAT AAT TGT TTA AGT AAC CCT GAA 25                  30                  35                  40
Val Glu Val Leu Gly Gly Glu Arg Ile Glu Thr Gly Tyr Thr Pro Ile Asp Ile Ser Leu
GTA GAA GTA TTA GGA GAA AGA ATA GAA ACT GGT TAC ACC CCA ATC GAT ATT TCC TTG 45                  50                  55                  60
Ser Leu Thr Gln Phe Leu Leu Ser Glu Phe Val Pro Gly Ala Gly Phe Val Leu Gly Leu
TCG CTA ACG CAA TTT CTT TTG AGT GAA TTT GTT CCC GGT GCT GGA TTT GTG TTA GGA CTA 65                  70                  75                  80
Val Asp Ile Ile Trp Gly Ile Phe Gly Pro Ser Gln Trp Asp Ala Phe Leu Val Gln Ile
GTT GAT ATA ATT TGG GGA ATT TTT GGT CCC TCT CAA TGG GAC GCA TTT CTT GTA CAA ATT
```

```
                    85                  90                  95                  100
Glu Gln Leu Ile Asn Gln Arg Ile Glu Glu Phe Ala Arg Asn Gln Ala Ile Ser Arg Leu
GAA CAG TTA ATT AAC CAA AGA ATA GAA GAA TTC GCT AGG AAC CAA GCC ATT TCT AGA TTA 105                 110                 115                 120
Glu Gly Leu Ser Asn Leu Tyr Gln Ile Tyr Ala Glu Ser Phe Arg Glu Trp Glu Ala Asp
GAA GGA CTA AGC AAT CTT TAT CAA ATT TAC GCA GAA TCT TTT AGA GAG TGG GAA GCA GAT 125                 130                 135                 140
Pro Thr Asn Pro Ala Leu Arg Glu Met Arg Ile Gln Phe Asn Asp Met Asn Ser Ala
CCT ACT AAT CCA GCA TTA AGA GAA ATG CGT ATT CAA TTC AAT GAC ATG AAC AGT GCC 145                 150                 155                 160
Leu Thr Thr Ala Ile Pro Leu Leu Ala Val Gln Asn Tyr Gln Val Pro Leu Leu Ser Val
CTT ACA ACC GCT ATT CCT CTT TTG GCA GTT CAA AAT TAT CAA GTT CCT CTT TTA TCA GTA
```

Figure 4B

```
                    165             170             175             180
Tyr Val Gln Ala Asn Leu His Leu Ser Val Leu Arg Asp Val Ser Phe Gly Gln
TAT GTT CAA GCT AAT TTA CAT TTA TCA GTT TTG AGA GAT GTT TCA TTT GGA CAA 185             190             195             200
Arg Trp Gly Phe Asp Ala Ala Thr Ile Asn Ser Arg Tyr Asn Asp Leu Thr Arg Leu Ile
AGG TGG GGA TTT GAT GCC GCG ACT ATC AAT AGT CGT TAT AAT GAT TTA ACT AGG CTT ATT 205             210             215             220
Gly Asn Tyr Thr Asp Tyr Ala Val Arg Trp Tyr Asn Thr Gly Leu Glu Arg Val Trp Gly
GGC AAC TAT ACA GAT TAT GCT GTA CGC TGG TAC AAT ACG GGA TTA GAA CGT GTA TGG GGA 225             230             235             240
Pro Asp Ser Arg Asp Trp Val Arg Tyr Asn Gln Phe Arg Arg Glu Leu Thr Leu Thr Val
CCG GAT TCT AGA GAT TGG GTA AGG TAT AAT CAA TTT AGA AGA GAA TTA ACA CTA ACT GTA
```

Figure 4C

```
                        245             250             255             260
Leu Asp Ile Val Ala Leu Phe Pro Asn Tyr Asp Ser Arg Arg Tyr Pro Ile Arg Thr Val
TTA GAT ATC GTT GCT CTG TTC CCG AAT TAT GAT AGT AGA AGA TAT CCA ATT CGA ACA GTT 265             270             275             280
Ser Gln Leu Thr Arg Glu Ile Tyr Thr Asn Pro Val Leu Glu Asn Phe Asp Gly Ser Phe
TCC CAA TTA ACA AGA GAA ATT TAT ACA AAC CCA GTA TTA GAA AAT TTT GAT GGT AGT TTT 285             290             295             300
Arg Gly Ser Ala Gln Gly Ile Glu Arg Ser Ile Arg Ser Pro His Leu Met Asp Ile Leu
CGA GGC TCG GCT CAG GGC ATA GAA AGA AGT ATT AGG AGT CCA CAT TTG ATG GAT ATA CTT 305             310             315             320
Asn Ser Ile Thr Ile Tyr Thr Asp Ala His Arg Gly Tyr Tyr Tyr Trp Ser Gly His Gln
AAC AGT ATA ACC ATC TAT ACG GAT GCT CAT AGG GGT TAT TAT TGG TCA GGG CAT CAA
```

Figure 4D

```
                    325                 330                 335                 340
Ile Met Ala Ser Pro Val Gly Phe Ser Gly Pro Glu Phe Thr Pro Leu Tyr Gly Thr
ATA ATG GCT TCT CCT GTC GGT TTT TCG GGG CCA GAA TTC ACG CCG CTA TAT GGA ACC 345                 350                 355                 360
Met Gly Asn Ala Ala Pro Gln Gln Arg Ile Val Ala Gln Leu Gly Gln Gly Val Tyr Arg
ATG GGA AAT GCA GCT CCA CAA CAA CGT ATT GTT GCT CAA CTA GGT CAG GGC GTG TAT AGA 365                 370                 375                 380
Thr Leu Ser Ser Thr Phe Tyr Arg Arg Pro Phe Asn Ile Gly Ile Asn Asn Gln Gln Leu
ACA TTA TCC TCT ACT TTT TAT AGA AGA CCT TTT AAT ATA GGG ATA AAT CAA CAA CTA 385                 390                 395                 400
Ser Val Leu Asp Gly Thr Glu Phe Ala Tyr Gly Thr Ser Ser Asn Leu Pro Ser Ala Val
TCT GTT CTT GAC GGG ACA GAA TTT GCT TAT GGA ACC TCA AAT TTG CCA TCC GCT GTA
```

Figure 4E

```
                                405                      410                      415                 420
Tyr Arg Lys Ser Gly Thr Val Asp Ser Leu Asp Glu Ile Pro Gln Asn Asn Val
TAC AGA AAA AGC GGA ACG GTA GAT TCG CTG GAT GAA ATA CCA CAG AAT AAC GTG 425                      430                      435                 440
Pro Pro Arg Gln Gly Phe Ser His Arg Leu Ser His Val Ser Met Phe Arg Ser Gly Ser
CCA CCT AGG CAA GGA TTT AGT CAT CGA TTA AGC CAT GTT TCA ATG TTT CGT TCA GGC TCT 445                      450                      455                 460
Ser Ser Val Ser Ile Ile Arg Ala Pro Met Phe Ser Trp Ile His Arg Ser Ala Glu
AGT AGT GTA AGT ATA ATA AGA GCT CCT ATG TTC TCT TGG ATA CAT CGT AGT GCT GAA 465                      470                      475                 480
Phe Asn Asn Ile Ile Ala Ser Asp Ser Ile Thr Gln Ile Pro Ala Val Lys Gly Asn Phe
TTT AAT AAT ATA ATT GCA TCG GAT AGT ATT ACT CAA ATC CCT GCA GTG AAG GGA AAC TTT
```

Figure 4F

```
Leu Phe Asn Gly Ser Val Ile Ser Gly Asp Leu Val Arg Leu
              485              495     500
CTT TTT AAT GGT TCT GTA ATT TCA GGA GAC TTA GTT AGA TTA

Asn Ser Ser Gly Tyr Ile Gln Asn Arg Gly Tyr Ile Glu Val Pro Ile His Phe Pro
              505              515              520
AAT AGT AGT GGA TAT ATT CAG AAT AGA GGG TAT ATT GAA GTT CCA ATT CAC TTC CCA

Ser Thr Ser Thr Arg Tyr Arg Val Arg Val Arg Tyr Ala Ser Val Thr Pro Ile His Leu
              525              535              540
TCG ACA TCT ACC AGA TAT CGA GTT CGT GTA CGG TAT GCT TCT ACC CCG ATT CAC CTC

Asn Val Asn Trp Gly Asn Ser Ser Ile Phe Ser Asn Thr Val Pro Ala Thr Ala Thr Ser
              545              555              560
AAC GTT AAT TGG GGT AAT TCA TCC ATT TTT TCC AAT ACA GTA CCA GCT ACA GCT ACG TCA

Leu Asp Asn Leu Gln Ser Ser Asp Phe Gly Tyr Phe Glu Ser Ala Asn Ala Phe Thr Ser
              565              575              580
TTA GAT AAT CTA CAA TCA AGT GAT TTT GGT TAT TTT GAA AGT GCC AAT GCT TTT ACA TCT
```

Figure 4G

```
                                    585             590             595             600
Ser Leu Gly Asn Ile Val Gly Val Arg Asn Phe Ser Gly Thr Ala Gly Val Ile Ile Asp
TCA TTA GGT AAT ATA GTA GGT GTT AGA AAT TTT AGT GGG ACT GCA GGA GTG ATA ATA GAC 605             610             615             620
Arg Phe Glu Ile Pro Val Thr Ala Thr Leu Glu Ala Tyr Asn Leu Glu Arg Ala
AGA TTT GAA ATT CCA GTT ACT GCA ACA CTC GAG GCT TAT AAT CTG GAA AGA GCG 625             630             635             640
Gln Lys Ala Val Asn Ala Leu Phe Thr Ser Thr Asn Gln Leu Gly Leu Lys Thr Asn Val
CAG AAG GCG GTG AAT GCG CTG TTT ACG TCT ACA AAC CAA CTA GGG CTA AAA ACA AAT GTA 645             650             655             660
Thr Asp Tyr His Ile Asp Gln Val Ser Asn Leu Val Thr Tyr Leu Ser Asp Glu Phe Cys
ACG GAT TAT CAT ATT GAT CAA GTG TCC AAT TTA GTT ACG TAT TTA TCG GAT GAA TTT TGT
```

Figure 4H

```
                665              670              675              680
Leu Asp Glu Lys Arg Glu Leu Ser Glu Lys Val Lys His Ala Lys Arg Leu Ser Asp Glu
CTG GAT GAA AAG CGA GAA TTG TCC GAG AAA GTC AAA CAT GCG AAG CGA CTC AGT GAT GAA 685              690              695              700
Arg Asn Leu Leu Gln Asp Ser Asn Phe Lys Asp Ile Asn Arg Gln Pro Glu Arg Gly Trp
CGC AAT TTA CTC CAA GAT TCA AAT TTC AAA GAC ATT AAT AGG CAA CCA GAA CGT GGG TGG 705              710              715              720
Gly Gly Ser Thr Thr Ile Gly Gly Asp Asp Val Phe Lys Glu Asn Tyr Val
GGC GGA AGT ACA ACC ATT ACC CAA GGA GAT GAC GTA TTT AAA GAA AAT TAC GTC 725              730              735              740
Thr Leu Ser Gly Thr Phe Asp Glu Cys Tyr Pro Thr Tyr Leu Tyr Gln Lys Ile Asp Glu
ACA CTA TCA GGT ACC TTT GAT GAG TGC TAT CCA ACA TAT TTG TAT CAA AAA ATC GAT GAA
```

Figure 4I

```
                    745                 750                 755                     760
Ser Lys Leu Lys Ala Phe Thr Arg Tyr Gln Leu Arg Gly Tyr Ile Glu Asp Ser Gln Asp
TCA AAA TTA AAA GCC TTT ACC CGT TAT CAA TTA AGA GGG TAT ATC GAA GAT AGT CAA GAC 765                 770                 775                     780
Leu Glu Ile Tyr Leu Ile Arg Tyr Asn Ala Lys His Glu Thr Val Asn Val Pro Gly Thr
TTA GAA ATC TAT TTA ATT CGC TAC AAT GCA AAA CAT GAA ACA GTA AAT GTG CCA GGT ACG 785                 790                 795                     800
Gly Ser Leu Trp Pro Leu Ser Ala Gln Ser Pro Ile Gly Lys Cys Gly Glu Pro Asn Arg
GGT TCC TTA TGG CCG CTT TCA GCC CAA AGT CCA ATC GGA AAG TGT GGA GAG CCG AAT CGA 805                 810                 815                     820
Cys Ala Pro His Leu Glu Trp Asn Pro Asp Leu Asp Cys Ser Cys Arg Asp Gly Glu Lys
TGC GCG CCA CAC CTT GAA TGG AAT CCT GAC TTA GAT TGT TCG TGT AGG GAT GGA GAA AAG
```

Figure 4J

```
                                    825                    830                    835                    840
Cys Ala His His Ser His Phe Ser Leu Asp Ile Asp Val Gly Cys Thr Asp Leu Asn
TGT GCC CAT CAT TCG CAT TTC TCC TTA GAC ATT GAT GTA GGA TGT ACA GAC TTA AAT 845                    850                    855                    860
Glu Asp Leu Gly Val Ile Phe Lys Ile Lys Thr Gln Asp Gly His Ala Arg Leu
GAG GAC CTA GGT GTA ATC TTT AAG ATT AAG ACG CAA GAT GGG CAC GCA AGA CTA 865                    870                    875                    880
Gly Asn Leu Glu Phe Leu Glu Lys Pro Leu Val Gly Glu Ala Leu Ala Arg Val Lys
GGG AAT CTA GAG TTT CTC GAA AAA CCA TTA GTA GGA GAA GCG CTA GCT CGT GTG AAA 885                    890                    895                    900
Arg Ala Glu Lys Lys Trp Arg Asp Lys Arg Glu Lys Leu Glu Trp Glu Thr Asn Ile Val
AGA GCG GAG AAA AAA TGG AGA GAC AAA CGT GAA AAA TTG GAA TGG GAA ACA AAT ATC GTT
```

Figure 4K

```
                                         905                      910                      915                      920
Tyr Lys Glu Ala Lys Glu Ser Val Asp Ala Leu Phe Val Asn Ser Gln Tyr Asp Gln Leu
TAT AAA GAG GCA AAA GAA TCT GTA GAT GCT TTA TTT GTA AAC TCT CAA TAT GAT CAA TTA 925                      930                      935                      940
Gln Ala Asp Thr Asn Ile Ala Met Ile His Ala Ala Asp Lys Arg Val His Ser Ile Arg
CAA GCG GAT ACG AAT ATT GCC ATG ATT CAT GCG GCA GAT AAA CGT GTT CAT AGC ATT CGA 945                      950                      955                      960
Glu Ala Tyr Leu Pro Glu Leu Ser Val Ile Pro Gly Val Asn Ala Ala Ile Phe Glu Glu
GAA GCT TAT CTG CCT GAG CTG TCT GTG ATT CCG GGT GTC AAT GCG GCT ATT TTT GAA GAA 965                      970                      975                      980
Leu Glu Gly Arg Ile Phe Thr Ala Phe Ser Leu Tyr Asp Ala Arg Asn Val Ile Lys Asn
TTA GAA GGG CGT ATT TTC ACT GCA TTC TCC CTA TAT GAT GCG AGA AAT GTC ATT AAA AAT
```

Figure 4L

```
                985                    990                    995                   1000
Gly Asp Phe Asn Asn Gly Leu Ser Cys Trp Asn Val Lys Gly His Val Asp Val Glu Glu
GGT GAT TTT AAT AAT GGC TTA TCC TGC TGG AAC GTG AAA GGG CAT GTA GAT GTA GAA GAA 1005                   1010                   1015                   1020
Gln Asn Gln Arg Ser Val Leu Val Pro Glu Trp Glu Ala Glu Val Ser Gln Glu
CAA AAC CAA CGT TCG GTC CTT GTT CCG GAA TGG GAA GCA GAA GTG TCA CAA GAA 1025                   1030                   1035                   1040
Val Arg Val Cys Pro Gly Arg Gly Tyr Ile Leu Arg Val Thr Ala Tyr Lys Glu Gly Tyr
GTT CGT GTC TGT CCG GGT CGT GGC TAT ATC CTT CGT GTC ACA GCG TAC AAG GAG GGA TAT 1045                   1050                   1055                   1060
Gly Glu Gly Cys Val Thr Ile His Glu Ile Glu Asn Asn Thr Asp Glu Leu Lys Phe Ser
GGA GAA GGT TGC GTA ACC ATT CAT GAG ATC GAG AAC AAT ACA GAC GAA CTG AAG TTT AGC
```

Figure 4M

```
                                            1065                    1070                    1075                    1080
Asn Cys Val Glu Glu Glu Ile Tyr Pro Asn Asn Thr Val Thr Cys Asn Asp Tyr Thr Val
AAC TGC GTA GAA GAG GAA ATC TAT CCA AAT AAC ACG GTA ACG TGT AAT GAT TAT ACT GTA 1085                    1090                    1095                    1100
Asn Gln Glu Gly Gly Ala Tyr Thr Ser Arg Asn Arg Gly Tyr Asn Glu Ala Pro
AAT CAA GAA GAA TAC GGA GGT GCG TAC ACT TCT CGT AAT CGA GGA TAT AAC GAA GCT CCT 1105                    1110                    1115                    1120
Ser Val Pro Ala Asp Tyr Ala Ser Val Tyr Glu Glu Lys Ser Tyr Thr Asp Gly Arg Arg
TCC GTA CCA GCT GAT TAT GCG TCA GTC TAT GAA GAA AAA TCG TAT ACA GAT GGA CGA AGA 1125                    1130                    1135                    1140
Glu Asn Pro Cys Glu Phe Asn Arg Gly Tyr Arg Asp Tyr Thr Pro Leu Pro Val Gly Tyr
GAG AAT CCT TGT GAA TTT AAC AGA GGG TAT AGG GAT TAC ACG CCA CTA CCA GTT GGT TAT
```

Figure 4N

```
                              1145            1150                  1155                   1160
Val Thr Lys Glu Tyr Phe Pro Glu Thr Asp Lys Val Trp Ile Glu Ile Gly Glu
GTG ACA AAA GAA TAC TTC CCA GAA ACC GAT AAG GTA TGG ATT GAG ATT GGA GAA
                 1165                   1170               1175
Thr Glu Gly Thr Phe Ile Val Asp Ser Val Glu Leu Leu Leu Met Glu Glu
ACG GAA GGA ACA TTT ATC GTG GAC AGC GTG GAA TTA CTC CTT ATG GAG GAA
```

Figure 40

PROCESS OF CONTROLLING LEPIDOPTERAN PESTS, USING *BACILLUS THURINGIENSIS* ISOLATE DENOTED *B.T* PS81GG

BACKGROUND OF THE INVENTION (1) Microbial Pesticides

The most widely used microbial pesticides are derived from the bacterium *Bacillus thuringiensis*. This bacterial agent is used to control a wide range of leaf-eating caterpillars, and mosquitos. *Bacillus thuringiensis* produces a proteinaceous paraspore or crystal which is toxic upon ingestion by a susceptible insect host. For example, *B. thuringiensis* var. kurstaki HD-1 produces a crystal called a delta toxin which is toxic to the larvae of a number of lepidopteran insects. The cloning and expression of this *B.t.* crystal protein gene in *Escherichia coli* has been described in the published literature (Schnepf, H. E. and Whitely, H. R. [1981] Proc. Natl. Acad. Sci. USA 78:2893-2897). U.S. Pat. No. 4,448,885 and U.S. Pat. No. 4,467,036 both disclose the expression of *B.t.* crystal protein in *E. coli*.

(2) Lepidopteran Pests

The beet armyworm (BAW) *Spodoptera exigua* is a widely distributed noctuid moth that attacks a broad range of field and vegetable crops. This economically important species originated in Asia, but is now found in many parts of the world including the United States.

The plants attacked by BAW include beets, peanuts, alfalfa, lettuce, asparagus, tomatoes, potatoes, corn, onions, peas, cotton, citrus, mallow, and even certain wild grasses. It is also a pest on ornamentals and floriculture crops, such as carnations and chrysanthemums. Larvae will feed on the leaves, stems, buds, and sometimes the roots of host plants. Heavy infestations can lead to complete defoliation of fields of a crop, such as table beets.

The female oviposits egg masses of about 80 eggs on the host plant foliage. These egg masses are covered with hairs and scales from the body of the female. An average of 500 to 600 eggs may be deposited over a 4 to 10 day period. Larvae hatch in 2 to 5 days and begin feeding on the foliage. Young larvae will feed in growing tips of the plant and developing buds, while older larvae are less discriminating, feeding on older foliage as well. The five larval instars take about 3 weeks to complete, at which time the mature larva drops to the ground and pupates in the soil. In the warmer parts of its range the BAW passes through four generations per year.

This species is generally considered to be difficult to control in various crop situations. Methomyl (Lannate) is commonly used to control this pest in lettuce and other field crops. However, resistance to methomyl has been reported in populations exposed to heavy use of this chemical (Yoshida and Parella [1987]). Consequently, there is a need to develop alternative control strategies for this important pest.

Another aspect of the use of broad spectrum materials like Lannate for BAW control is secondary pest outbreaks. This is the disruptive influence of a non-selective chemical on natural control agents of other pests in a given crop. In tomatoes, chrysanthemums, and other crops, where leaf miners can be a problem, the use of Lannate severely depresses populations of the natural enemies of the leafminers. With removal of leafminer parasites, the leafminers can build to very high population levels and cause severe damage.

The discovery and use of a novel *Bacillus thuringiensis* isolate with good activity against BAW is a distinct improvement in the control of this lepidopteran pest.

BRIEF SUMMARY OF THE INVENTION

The subject invention concerns a novel *Bacillus thuringiensis* isolate designated B.t. PS81GG which has activity against lepidopteran pests. It is highly active against the best armyworm (BAW).

The subject invention also includes mutants of B.t. PS81GG which are also active against lepidopteran pests.

Also disclosed and claimed is the novel toxin gene from the novel isolate. This toxin gene can be transferred to suitable hosts via a plasmid vector.

Specifically, the invention comprises a novel *B.t.* isolate denoted *B.t.* PS81GG, and mutants thereof, and a novel delta endotoxin gene which encodes a 133,156 dalton protein which is active against lepidopteran pests.

BRIEF DESCRIPTION OF THE DRAWINGS

FIGS. 2A through 2D show DNA encoding the novel toxin.

FIGS. 3A through 3E show the amino acid sequence of the novel toxin.

FIGS. 4A through 4D are a composite of FIGS. 2 and 3.

DETAILED DISCLOSURE OF THE INVENTION

Figure 1:
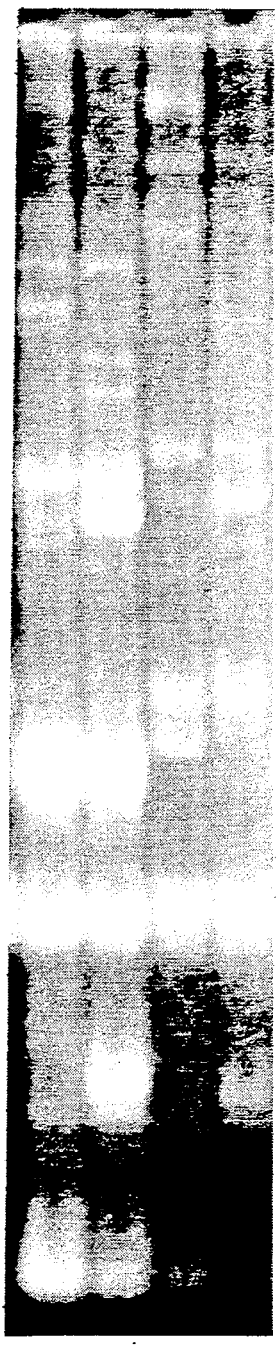
FIG. 1 is an agarose gel electrophoresis of plasmid preparations from *B.t.* PS81GG and *B.t.* HD-1.

The novel toxin gene of the subject invention was obtained from a novel lepidopteran-active *B. thuringiensis* (B.t.) isolate designated PS81GG.

Characteristics of *B.t.* PS81GG

Colony morphology—Large colony, dull surface, typical *B.t.*

Vegetative cell morphology—typical *B.t.*

Flagellar serotype—3a3b, kurstaki.

Intracellular inclusions—sporulating cells produce a bipyramidal crystal which partially encloses a smaller cuboidal crystal.

Plasmid preparations—agarose gel electrophoresis of plasmid preparations distinguishes *B.t.* PS81GG from *B.t.* HD-1 and other *B.t.* isolates.

Alkali-soluble proteins—*B.t.* PS81GG has a 130,000 dalton protein and a 60,000 dalton protein.

Unique toxin—the 130,000 dalton toxin is different from any previously identified.

Activity—*B.t.* PS81GG kills all Lepidoptera tested, and is twice as active against Beet Armyworm as *B.t.* HD-1.

Beet Armyworm assay results:

*B.t.* PS81GG LC50=4 ug/ml

*B.t.* HD-1 LC50=8 ug/ml

*Spodoptera exigua* Bioassay: Dilutions are prepared of a spore and crystal pellet, mixed with USDA Insect Diet (Technical Bulletin 1528, U.S. Department of Agriculture), and poured into small plastic trays. Neonate *Spodoptera exigua* larvae are placed on the diet mixture and held at 25° C. Mortality is recorded after six days.

*B. thuringiensis* PS81GG, NRRL B-18425, and mutants thereof, can be cultured using standard known media and fermentation techniques. Upon completion of the fermentation cycle, the bacteria can be harvested by first separating the *B.t.* spores and crystals from the fermentation broth by means well known in the art. The recovered *B.t.* spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains of *B. thuringiensis.* (HD-1) active against Lepidoptera, e.g., caterpillars. *B.t.* PS81GG, and mutants thereof, can be used to control lepidopteran pests.

A subculture of *B.t.* PS81GG and the *E. coli* host harboring the toxin gene of the invention, *E. coli* NRRL B-18428 was deposited in the permanent collection of the Northern Research Laboratory, U.S. Department of Agriculture, Peoria, Ill., USA on Oct. 19, 1988. The accession numbers are as follows:

*B.t.* PS81GG—NRRL B-18425; deposited Oct. 11, 1988.

*E. coli* (pMYC388)—NRRL B-18428; deposited Oct. 19, 1988.

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The toxin gene of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of lepidopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the *B.t.* toxin.

Where the *B.t.* toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species sucha s *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing the *B.t.* gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon(s), a terminator region, and optionally, a polyadenylation signal.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pR01614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The *B.t.* gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shigella, Salmonella, and Proteus; Bacillaceae; Rhizobiceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

Characteristics of particular interest in selecting a host cell for purposes of production include ease of introducing the *B.t.* gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis*, and the like.

The cell will usually be intact and be substantially in the proliferative form when treated, rather than in a spore form, although in some instances spores may be employed.

Treatment of the microbial cell, e.g., a microbe containing the *B.t.* toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17–80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the *B.t.* insecticidal gene may be grown in any convenient nutrient medium, where the DNA construct provides a selective advantage, providing for a selective medium so that substantially all or all of the cells retain the *B.t.* gene. These cells may then be harvested in accordance with conventional ways. Alternatively, the cells can be treated prior to harvesting.

The *B.t.* cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest(s), e.g., plants, soil or water, by spraying, dusting, sprinkling, or the like.

Mutants of PS81GG can be made by procedures well known in the art. For example, an asporogenous mutant can be obtained through ethylmethane sulfonate (EMS) mutagenesis of PS81GG. Other mutants can be made using ultraviolet light and nitrosoguanidine by procedures well known in the art.

Following are examples which illustrate procedures, including the best mode, for practicing the invention. These examples should not be construed as limiting. All percentages are by weight and all solvent mixture proportions are by volume unless otherwise noted.

EXAMPLE 1-CULTURING *B.t.* PS81GG, NRRL B-18425

A subculture of *B.t.* PS81GG, NRRL B-18425, or mutants thereof, can be used to inoculate the following medium, a peptone, glucose, salts medium.

| | |
|---|---|
| Bacto Peptone | 7.5 g/l |
| Glucose | 1.0 g/l |
| $KH_2PO_4$ | 3.4 g/l |
| $K_2HPO_4$ | 4.35 g/l |
| Salt Solution | 5.0 ml/l |
| $CaCl_2$ Solution | 5.0 ml/l |
| Salts Solution (100 ml) | |
| $MgSO_4.7H_2O$ | 2.46 g |
| $MnSO_4.H_2O$ | 0.04 g |
| $ZnSO_4.7H_2O$ | 0.28 g |
| $FeSO_4.7H_2O$ | 0.40 g |
| $CaCl_2$ Solution (100 ml) | |
| $CaCl_2.2H_2O$ | 3.66 g |
| pH 7.2 | |

The salts solution and CaCl2 solution are filter-sterilized and added to the autoclaved and cooked broth at the time of inoculation. Flasks are incubated at 30° C on a rotary shaker at 200 rpm for 64 hr.

The above procedure can be readily scaled up to large fermentors by procedures well known in the art.

The *B.t.* spores and/or crystals, obtained in the above fermentation, can be isolated by procedures well known in the art. A frequently-used procedure is to subject the harvested fermentation broth to separation techniques, e.g., centrifugation.

EXAMPLE 2—CLONING OF NOVEL TOXIN GENE AND TRANSFORMATION INTO ESCHERICHIA COLI

Total cellular DNA was prepared by growing the cells of *B. thuringiensis* HD-1 and the novel *B.t.* PS81GG to a low optical density ($OD_{600}=1.0$) and recovering the cells by centrifugation. The cells were protoplasted in TES buffer (30 mM Tris-Cl, 10 mM EDTA, 50 mM NaCl, pH=8.0) containing 20% sucrose and 50 mg/ml lysozyme. The protoplasts were lysed by addition of SDS to a final concentration of 4%. The cellular material was precipitated overnight at 4° C. in 100 mM final concentration neutral potassium chloride. The supernate was phenol/chloroform (1:1) extracted twice and the DNA precipitated in ethanol. The DNA was purified by isopycnic banding on a cesium chloride gradient.

Total cellular DNA from PS81GG and HD-1 was digested with EcoRI and separated by electrophoresis on a 0.8% Agarose-TAE-buffered gel. A Southern blot of the gel was probed with the NsiI to NsiI fragment of toxin gene contained in the plasmid pM1,130-7 of NRRL B-18332 and the NsiI to KpnI fragment of the "4.5 Kb class" toxin gene (Kronstad and Whitely, [1986]Gene USA 43:29-40). These two fragments were combined and used as the probe. Results show that hybridizing fragments of PS81GG are distinct from those cf HD-1. Specifically, a 3.0 Kb hybridizing band in PS81GG was detected instead of the 800 bp larger 3.8 Kb hybridizing band seen in HD-1.

Two hundred micrograms of PS81GG total cellular DNA was digested with EcoRI and separated by electrophoresis on a preparative 0.8% Agarose-TAE gel. The 2.5 to 3.5 Kb region of the gel was cut out and the DNA from it was electroeluted and concentrated using an ELUTIP TM -d (Schleicher and Schuell, Keene, N.H.) ion exchange column. The isolated EcoRI fragments were ligated to LAMBDA ZAP TM EcoRI arms (Stratagene Cloning Systems, La Jolla, Calif.) and packaged using GIGAPACK GOLD TM extracts. The packaged recombinant phage were plated out with *E. coli* strain BB4 (Stratagene) to give high plaque density. The plaques were screened by standard nucleic acid hybridization procedure with radiolabeled probe. The plaques that hybridized were purified and re-screened at a lower plaque density. The resulting purified phage were grown with R408 M13 helper phage (Stratagene) and the recombinant BLUESCRIPT TM (Stratagene) plasmid was automatically excised and packaged. The "phagemid" was re-infected in XLl-Blue *E. coli* cells (Stratagene) as part of the automatic excision process. The infected XLl-Blue cells were screened for ampicillin resistance and the resulting colonies were analyzed by standard miniprep procedure to find the desired plasmid. The plasmid, pM4,31-1, contained an approximate 3 0 Kb EcoRI insert which contained an internal EcoRI site. The cloned fragment was sequenced using Strategene's T7 and T3 primers plus a set of existing *B.t.* endotoxin oligonucleotide primers.

Total cellular PS81GG DNA was partially digested with AluI or RsaI and digests were mixed. DNA was modified with EcoRI methylase, EcoRI linkers were ligated onto ends, and excess linkers were removed by EcoRI digestion. DNA was size-fractionated on 0.8% Agarose-TAE gels and the approximately 4 to 8 Kb fragments were recovered by electroelution and NACS 52 column chromatography (BRL). Following insert ligation into LAMBDA ZAP TM (Stratagene) which was cut with EcoRI, DNA was packaged into phage heads. Libraries were screened by nucleic acid filter hybridization using a radiolabeled synthetic oligonucleotide probe (CCTGTCGGTTTTTCGGGGCC).

Hybridizing positives were plaque-purified and insert DNA was excised from phage DNA onto pBLUESCRIPT TM plasmid (Stratagene) with helper phage, according to manufacturers directions (Stratagene). The desired plasmid, pMYC388, was restriction mapped and the *B.t.* toxin coding sequence fully characterized by DNA sequencing.

Data from standard insect tests show that the novel *B.t.* PS81GG is active against all Lepidoptera tested.

The above cloning procedures were conducted using standard procedures unless otherwise noted.

The various methods employed in the preparation of the plasmids and transformation of host organisms are well known in the art. Also, methods for the use of lambda bacteriophage as a cloning vehicle, i.e., the preparation of lambda DNA, in vitro packaging, and transfection of recombinant DNA, are well known in the art. These procedures are all described in Maniatis, T., Fritsch, E. F., and Sambrook, J. (1982) *Molecular Cloning: A Laboratory Manual*, Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, Md., or New England Biolabs, Beverly, Mass. The enzymes are used according to the instructions provided by the supplier.

Plasmid pMYC388 containing the *B.t.* toxin gene, can be removed from the transformed host microbe by use of standard well-known procedures. For example, *E. coli* (pMYC388) NRRL B-18428 can be subjected to cleared lysate isopycnic density gradient procedures, and the like, to recover pMYC388.

EXAMPLE 3—INSERTION OF TOXIN GENE INTO PLANTS

The novel gene coding for the novel insecticidal toxin, as disclosed herein, can be inserted into plant cells using the Ti plasmid from *Agrobacter tumefaciens*. Plant cells can then be caused to regenerate into plants (Zambryski, P., Joos, H., Gentello, C., Leemans, J., Van Montague, M. and Schell, J [1983] Cell 32:1033-1043). A particularly useful vector in this regard is pEND4K (Klee, H. J., Yanofsky, M. F. and Nester, E. W. [1985] Bio/Technology 3:637-642). This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells.

EXAMPLE 4—CLONING OF NOVEL *b. THURINGIENSIS* GENE INTO BACULOVIRUSES

The novel gene of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399–406), and pAC380, described by Smith et al. (Smith, G. E., Summers, M. D. and Fraser, M. J. [1983] Mol Cell. Biol. 3:2156-2165). The gene coding for the novel protein toxin of the invention can be modified with BamHI linkers at appropriate regions both upstream and downstream from the coding region and inserted into the passenger site of one of the AcNPV vectors.

As disclosed previously, the nucleotide sequence encoding the novel B.t. toxin gene is shown in FIG. 2. The deduced amino acid sequence is shown in FIG. 3.

It is well known in the art that the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.
A = adenine
G = guanine
C = cytosine
T = thymine
X = T or C if Y is A or G
X = C if Y is C or T
Y = A, G, C or T if X is C
Y = A or G if X is T
W = C or A if Z is A or G
W = C if Z is C or T
Z = A, G, C or T if W is C
Z = A or G if W is A
QR = TC if S is A, G, C or T; alternatively
QR = AG if S is T or C
J = A or G
K = T or C
L = A, T, C or G
M = A, C or T The above shows that the novel amino acid sequence of the B.t. toxin can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249-255). Thus, the subject invention includes mutants of the amino acid sequence depicted herein which do not alter the protein secondary structure, or if the structure is altered, the biological activity is retained to some degree.

We claim:

1. A process for controlling lepidopteran insect pests which comprises contacting said insect pests with an insect-controlling effective amount of B. thuringiensis PS81GG having all the identifying characteristics of NRRL B-18425, or mutants thereof, which retain the property of being active against lepidopteran insects.

2. The process, according to claim 1, wherein said insect pests belong to the order Lepidoptera.

3. The process, according to claim 2, wherein said insect pest is the beet armyworm.

4. The process, according to claim 1, wherein said insect pest is contacted with an insect-controlling effective amount of B. thuringiensis PS81GG, by incorporating said B. thuringiensis PS81GG into a bait granule and placing said granule on or in the soil when planting seed of a plant upon which plant insect pest is known to feed.

5. A process for controlling soil-inhabiting insect pests of the order Lepidoptera which comprises
   (1) preparing a bait granule comprising B. thuringiensis PS81GG spores or crystals, or mutants thereof, which retain the property of being active against lepidopteran insects; and
   (2) placing said bait granule on or in the soil.

6. The process, according to claim 5, wherein said bait granule is applied at the same time corn seed is planted in the soil.

7. The process, according to claims 1 or t, wherein substantially intact B.t. PS81GG cells, or mutants thereof, which retain the property of being active against lepidopteran insects are treated to prolong the pesticidal activity when the substantially intact cells are applied to the environment of a target pest.

8. A composition of matter comprising B. thuringiensis PS81GG spores or crystals, or mutants thereof, which retain the property of being active against lepidopteran insects, in association with an insecticide carrier.

9. The composition of matter, according to claim 8, wherein said carrier comprises phagostimulants or attractants.

10. A composition of matter comprising B. thuringiensis PS81GG, or mutants thereof, which retain the property of being active against lepidopteran insects, in association with formulation ingredients applied as a seed coating.

11. Bacillus thuringiensis PS81GG, having all the identifying characteristics of NRRL B-18425, or mutants thereof, which retain activity against insect pests of the order Lepidoptera.

* * * * *

UNITED STATES PATENT AND TRADEMARK OFFICE
CERTIFICATE OF CORRECTION

PATENT NO. : 5,169,629

DATED : December 8, 1992

INVENTOR(S) : Jewel M. Payne, August J. Sick and Mark Thompson

It is certified that error appears in the above-indentified patent and that said Letters Patent is hereby corrected as shown below:

Column 2    line 11:  Delete "best" and insert --beet--.

Column 4    line 19:  After "*Methylophilius*" insert --*Agrobacterium*--.

Column 8    line 19:  Delete "102" and insert --$10^2$--.

Column 8    line 58:  Delete "CaCl2" and insert --$CaCl_2$--.

Column 9    line 57:  Delete "30 Kb" and insert --3.0 Kb--.

Column 12   line 37:  Delete "to claims 1 or t" and insert --to claims 1 or 5--.

Signed and Sealed this

Fourteenth Day of December, 1993

Attest:

BRUCE LEHMAN

*Attesting Officer*        Commissioner of Patents and Trademarks